US010309902B2

(12) United States Patent
Simpson et al.

(10) Patent No.: US 10,309,902 B2
(45) Date of Patent: Jun. 4, 2019

(54) CHARACTERIZATION OF TRACE CRYSTALLINITY BY SECOND HARMONIC GENERATION MICROSCOPY

(71) Applicant: Purdue Research Foundation, West Lafayette, IN (US)

(72) Inventors: Garth Jason Simpson, West Lafayette, IN (US); Paul David Schmitt, Zionsville, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 15/514,893

(22) PCT Filed: Sep. 28, 2015

(86) PCT No.: PCT/US2015/052604
§ 371 (c)(1),
(2) Date: Mar. 28, 2017

(87) PCT Pub. No.: WO2016/049623
PCT Pub. Date: Mar. 31, 2016

(65) Prior Publication Data
US 2017/0212053 A1    Jul. 27, 2017

Related U.S. Application Data

(60) Provisional application No. 62/056,605, filed on Sep. 28, 2014.

(51) Int. Cl.
*G01N 21/00* (2006.01)
*G01N 21/65* (2006.01)
(Continued)

(52) U.S. Cl.
CPC .......... *G01N 21/65* (2013.01); *G01N 21/636* (2013.01); *G01N 23/207* (2013.01); *G01N 2223/606* (2013.01); *G01N 2223/612* (2013.01)

(58) Field of Classification Search
CPC ... G01J 3/02; G01J 3/44; G01N 21/65; G01N 21/68; G01N 23/207; G01N 2021/656; G01N 33/28
See application file for complete search history.

(56) References Cited

U.S. PATENT DOCUMENTS

| 2003/0106492 A1* | 6/2003 | Levinson | B01J 19/0046 117/200 |
| 2003/0123057 A1* | 7/2003 | Lemmo | B01J 19/0046 356/301 |

(Continued)

OTHER PUBLICATIONS

Saldin et al., Structure of a single particle from scattering by many particles randomly oriented about an axis: toward structure solution without crystallization,Mar. 2010, New Journal of Physics. 31.*

*Primary Examiner* — Abdullahi Nur
(74) *Attorney, Agent, or Firm* — Purdue Research Foundation

(57) ABSTRACT

A method for quantifying crystallinity within a sample using second harmonic generation microscopy is described herein. In one aspect, a method for reducing the timeframe for accelerated stability testing of amorphous solid dispersions of active pharmaceutical ingredients though identifying regions of interest to quantify crystallinity and composition is presented herein.

8 Claims, 9 Drawing Sheets

(51) Int. Cl.
*G01N 23/207* (2018.01)
*G01N 21/63* (2006.01)

(56) References Cited

U.S. PATENT DOCUMENTS

| | | | | |
|---|---|---|---|---|
| 2006/0141533 A1* | 6/2006 | Levinson | ................ | C12Q 1/18 435/7.1 |
| 2010/0294949 A1* | 11/2010 | Sasaki | ................ | G02B 21/0076 250/458.1 |
| 2014/0091012 A1* | 4/2014 | Ros | ........................ | B03C 5/005 209/129 |

* cited by examiner

FIG. 2a
FIG. 2b
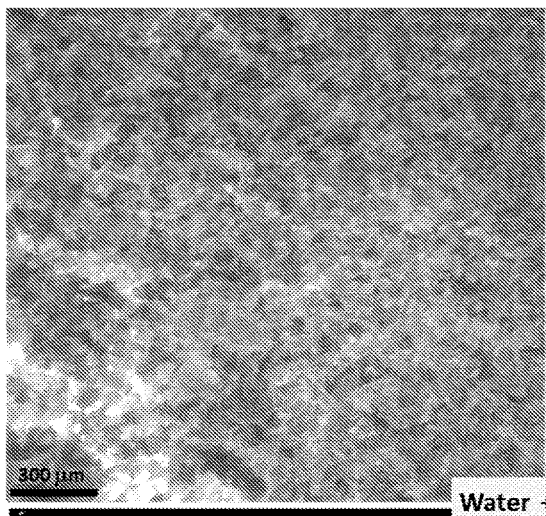
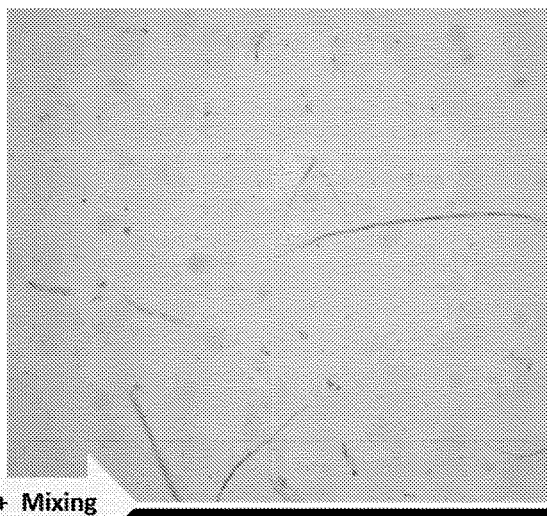
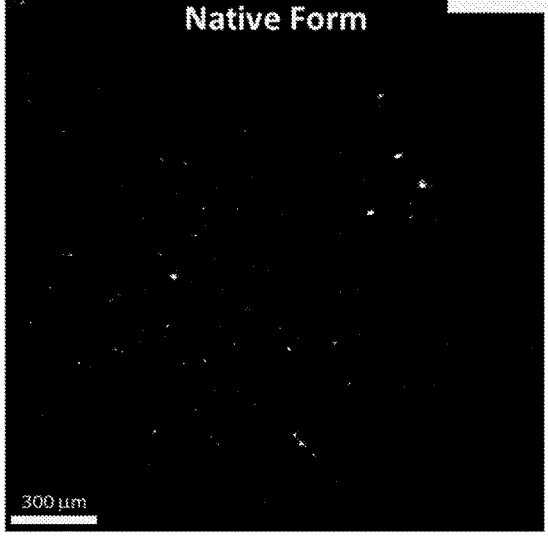
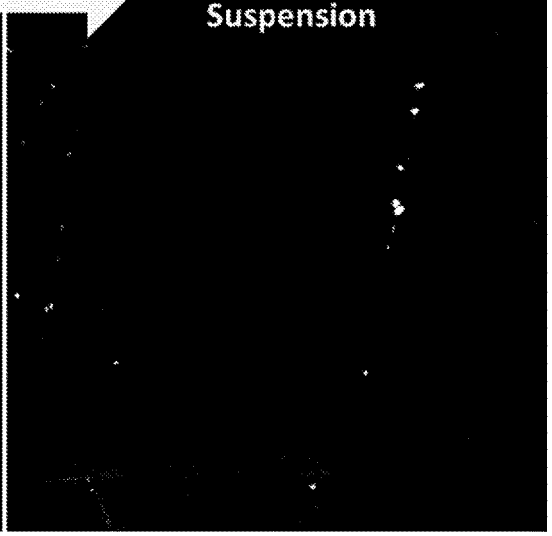
FIG. 2c
FIG. 2d

CHARACTERIZATION OF TRACE CRYSTALLINITY BY SECOND HARMONIC GENERATION MICROSCOPY

CROSS-REFERENCE TO RELATED APPLICATIONS

The present patent application is a 35 U.S.C. § 371 national phase application of PCT/US15/52604, filed Sep. 28, 2015, which is related to and claims the priority benefit of U.S. Provisional Patent Application Ser. No. 62/056,605, filed Sep. 28, 2014, the contents of which is hereby incorporated by reference in its entirety into this disclosure.

STATEMENT OF GOVERNMENT INTEREST

This invention was made with government support under FD-U-004275 awarded by the Food and Drug Administration, NIH #GM103910 awarded by the National Institutes of Health, and DE-SC0000997 awarded by the U.S. Department of Energy. The government has certain rights in the invention.

TECHNICAL FIELD

The present disclosure generally relates to quantifying crystallinity, and in particular to a method that uses second harmonic generation microscopy to rapidly identify regions of interest for localized confocal Raman spectroscopy and X-ray diffraction (XRD) measurements with a narrow source in order to quantify crystallinity.

BACKGROUND

This section introduces aspects that may help facilitate a better understanding of the disclosure. Accordingly, these statements are to be read in this light and are not to be understood as admissions about what is or is not prior art.

Modern drug discovery frequently identifies active pharmaceutical ingredients (APIs) that are highly effective against the disease target, but which are hard to deliver to the body. Increasingly, new compounds have suboptimal aqueous solubility, whereby it is estimated that some 40% of new chemical entities are discarded for this reason. Solubilization strategies are therefore essential. One of the most common methods towards this end is the creation of amorphous formulations, which requires kinetically trapping the API in a non-crystalline metastable form to increase the dissolution rate and transient concentration. Unfortunately, such formulations run the risk of spontaneously transitioning to their more thermodynamically stable crystalline form. If such phase changes occur, significant reductions in drug bioavailability may arise.

For intravenous (IV) formulations in particular, it is essential to be able to either completely dissolve the drug in a physiologically compatible vehicle, or to administer a suspension with particles small enough so that they will not occlude blood vessels. Therefore, various different strategies to solubilize APIs are employed, including pH adjustment, the use of cosolvents, surfactants, and emulsifiers, and most recently nanosuspensions. Unfortunately, additives used to solubilize drugs for IV formulations can cause toxicity, in some cases fatal. Therefore, solubilization strategies that minimize the use of potentially toxic additives are of great interest. One interesting example of a poorly water soluble drug that was reformulated to avoid toxicity issues and to improve efficacy is paclitaxel, a vital anticancer drug with activity against several human cancers. The original formulation contained the drug solubilized in ethanol and polyethoxylated castor oil, however, the solubilizing vehicle contributed to serious hypersensitivity reactions. An alternative formulation was subsequently developed whereby paclitaxel was coprecipitated with human serum albumin leading to an amorphous formulation. Upon reconstitution, this formulation is a nanosuspension containing particles of 120 nm.

Quantification and detection of crystallinity at low levels within an amorphous formulation is often a defining measurement for predicting the long-term success of the formulation. Crystal formation is detrimental because it not only reduces the solubility advantage of the amorphous formulation, but the presence of large particulates in IV formulations is problematic and hence subject to stringent regulations. Unfortunately for potent APIs at low loadings, accurate determination of crystallinity poses a significant measurement challenge. As the drug loading approaches the detection limits of conventional bench top methods, even major differences in relative drug crystallinity become difficult to distinguish with statistical confidence. Commonly used methods for crystal detection in the drug formulation pipeline include X-ray powder diffraction (PXRD), differential scanning calorimetry (DSC), Raman spectroscopy, scanning electron microscopy, hot stage microscopy, and nuclear magnetic resonance spectroscopy (NMR). However, none of these techniques typically exhibit detection limits for crystallinity significantly lower than ~1%, in most cases because of background noise from the much larger non-crystalline fraction.

Nonlinear optical (NLO) microscopy, in particular second harmonic generation (SHG), has recently emerged as a complementary technique for the rapid detection and quantification of trace crystallinity within pharmaceutical materials. Coherent SHG selectively arises exclusively from the bulk crystalline fraction and only within crystals of appropriate symmetry. The chirality inherent in most new pharmaceutical APIs largely guarantees that the crystals produced will be bulk-allowed for SHG. This selectivity for crystalline API has allowed measurements with detection limits on the order of parts per billion to as low as parts per trillion ranges under favorable conditions.

Despite the low detection limits of SHG microscopy, the SHG intensity itself provides little significant chemical information about the composition of the SHG-active source. In the present disclosure, efforts were undertaken to lower the detection limits of both Raman and XRD through background suppression, guided by SHG imaging. In brief, targeting Raman and XRD analysis to regions of interest identified by SHG minimizes the volume of additional material contributing to the signal and greatly reduces the background from the amorphous material.

There is therefore an unmet need to lower the detection limits of both Raman and XRD.

SUMMARY

In one aspect, a method for reducing the timeframe for accelerated stability testing of amorphous solid dispersions of active pharmaceutical ingredients though identifying regions of interest to quantify crystallinity and composition is presented herein. The method includes the steps of acquiring at least one second harmonic generation (SHG) image of a sample, analyzing the at least one SHG image to obtain at least one field of view of interest, generating a plurality of particle histograms from the at least one field of view, locating at least one specific field of view containing a region of interest within the sample, acquiring at least one Raman spectrum from the identified region or regions of interest in the sample, assessing composition of a crystallite via spectral analysis from the Raman measurements, acquiring x-ray diffraction (XRD) images from the identified region or regions of interest in the sample, producing XRD patterns from the XRD images, generating representative powder patterns from a representative sample, and comparing the powder patterns from the representative sample with a set of powder patterns from the sample to thereby identify regions of interest to assess composition of a crystallite. In another aspect, the XRD patters are produced using mean-subtracted autocorrelation of the XRD image along the azimuthal axis. In another aspect, the method also includes the step of collecting SHG light in the transmission direction.

BRIEF DESCRIPTION OF DRAWINGS

FIG. 2a is a brightfield image of ABRAXANE® before dissolution in ultra-pure water followed by rigorous mixing.

FIG. 2b is a brightfield image of ABRAXANE® after dissolution in ultra-pure water followed by rigorous mixing.

FIG. 2c is a SHG image of ABRAXANE® before dissolution in ultra-pure water followed by rigorous mixing.

FIG. 2d is a SHG image of ABRAXANE® after dissolution in ultra-pure water followed by rigorous mixing.

DETAILED DESCRIPTION

Figure 1B:
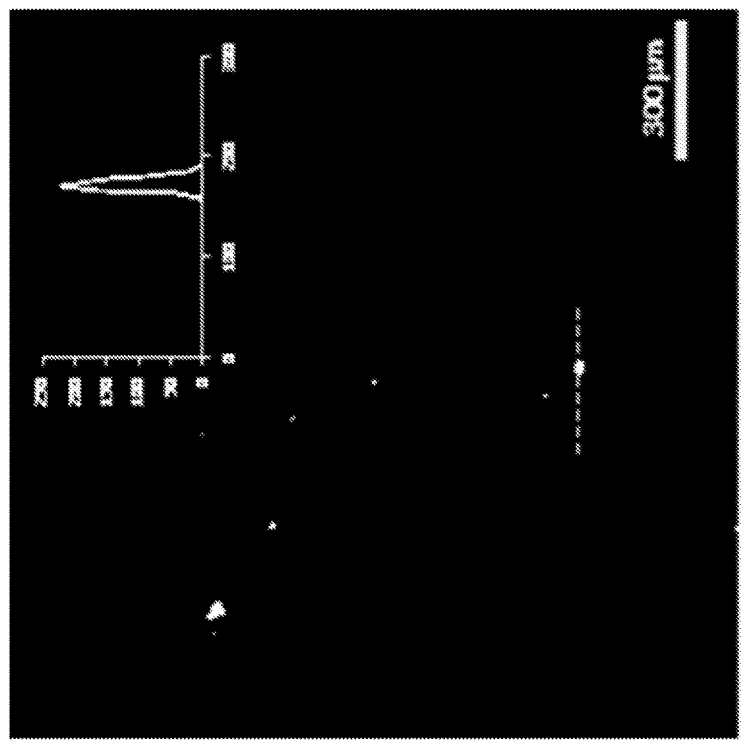
FIG. 1b is a SHG microscopy image of batch 2 of ABRAXANE®.
Figure 1A:
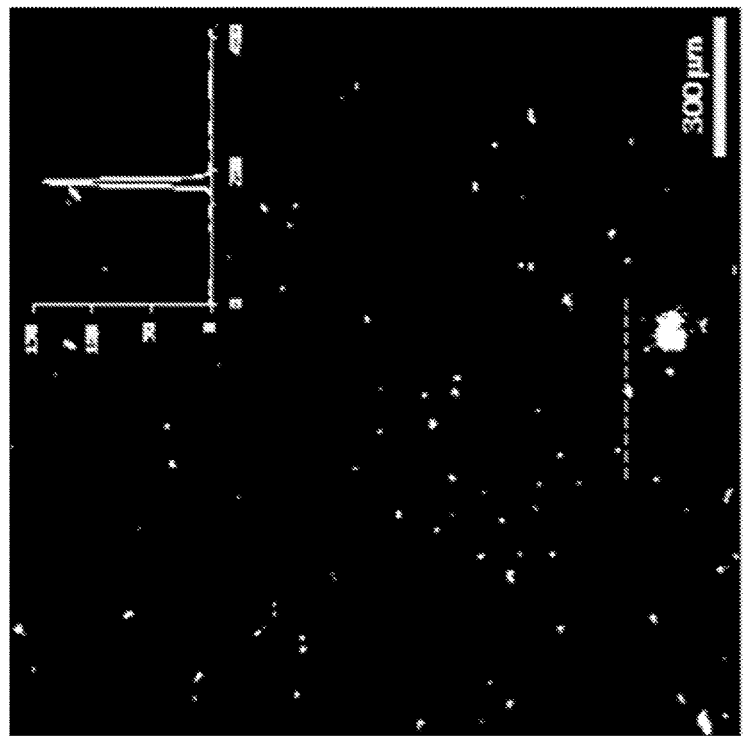
FIG. 1a is a second harmonic generation (SHG) microscopy image of batch 1 of ABRAXANE®.
Figure 1D:
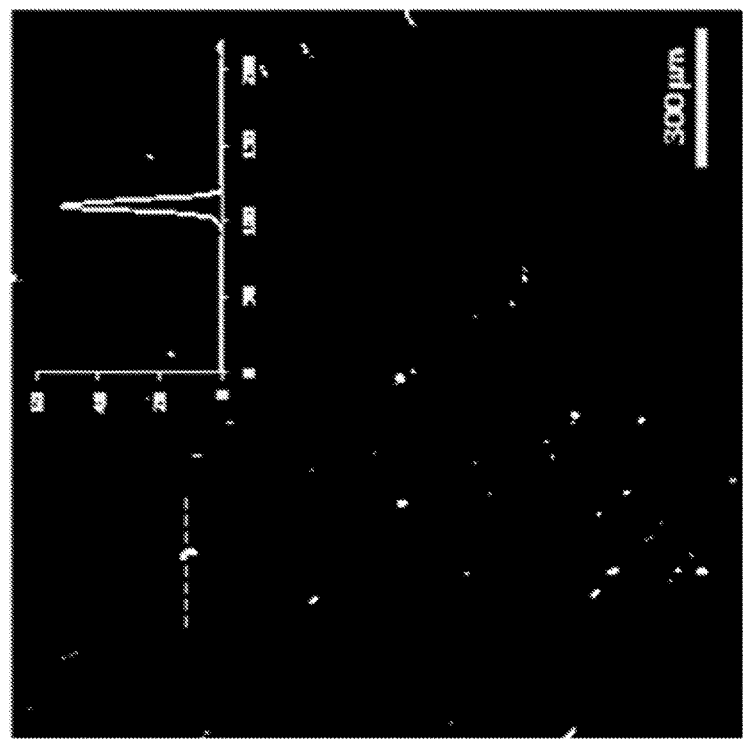
FIG. 1d is a SHG microscopy image of batch 4 of ABRAXANE®.
Figure 1C:
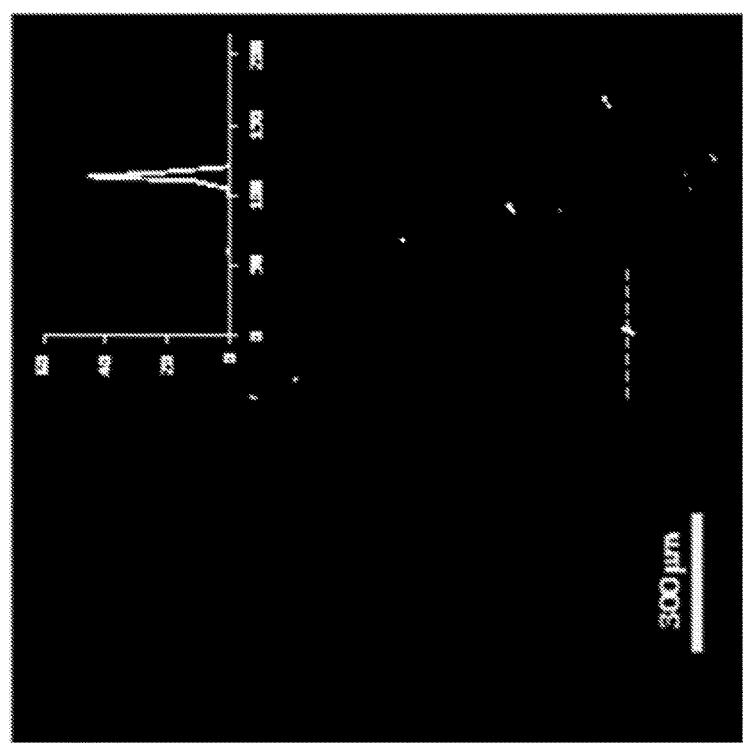
FIG. 1c is a SHG microscopy image of batch 3 of ABRAXANE®.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Presented herein is a method to lower the detection limits of both Raman and XRD through background suppression, guided by SHG imaging. In brief, targeting Raman and XRD analysis to regions of interest identified by SHG minimizes the volume of additional material contributing to the signal and greatly reduces the background from the amorphous material.

In the present disclosure, assessment of this SHG-guided analysis approach was performed for the amorphous IV formulation ABRAXANE® (nanoparticle albumin bound paclitaxel for injectable suspension). It should be appreciated that although ABRAXANE® was used in the example presented herein, such use is not intended to be limiting on the applicability of the herein disclosed methods. As such, any amorphous formulations and amorphous dispersion can benefit from the herein described methods, including but not limited to products made from techniques such as lyophilization, spray-drying, and hot-melt extrusion, among other examples. In addition, the drug/excipient combinations are also not meant to be limited to those mentioned herein.

ABRAXANE® was the first nanosuspension approved for clinical use, and is indicated to contain 10% (w/w) paclitaxel (PTX) bound to nanoparticles of human serum albumin (HSA). ABRAXANE® has been shown to have increased efficacy compared to other PTX formulations (e.g., Taxol®), particularly in the treatment of breast cancer, non-small cell lung cancer, and pancreatic carcinoma. PTX is generally regarded as exhibiting substantial solubility limitations, with crystalline PTX exhibiting poor bioavailability. In addition to the increased apparent solubility arising from an amorphous nanosuspension, it is thought that ABRAXANE® achieves higher treatment specificity as a result of its HSA matrix, utilizing the known high protein uptake rate of tumors.

Methods

ABRAXANE® samples were analyzed in their native (solid) form as obtained from the manufacturer. Four different batches were imaged (lot numbers: 6106359, 6106934, 6107014, and 6107321, batches 1-4 respectively). SHG images were acquired with a commercial SONICC (second-order nonlinear optical imaging of chiral crystals) microscope (Formulatrix, Inc.). The system contains a Fianium FemtoPower laser (1060 nm, 1.3 W power output), with a 51 MHz repetition rate and a 166 fs pulse width. The instrument uses resonant mirror/galvanometer beam scanning (8 kHz fast axis) to generate images. Unless otherwise stated, all SONICC images were acquired with 250 mW infrared IR power at the sample, with a 2 second image acquisition time. SHG light was collected in the transmission direction, requiring the preparation of thin samples to minimize scattering losses. In brief, samples were prepared by placing a small aliquot of powder between two glass coverslips, within a thin (~100 µm) spacer to ensure uniform sample thickness. 12 fields of view were obtained for each sample and used to generate particle histograms. The fraction imaged by SHG represents approximately 1% of the 1 g bulk sample, and a total volume probed of 2.2 mm³ (12 fields of view with dimensions of 1925 µm×1925 µm×50 µm). For analysis of relative PTX crystallinity in batch 1, physical mixtures of crystalline PTX in HSA (Attix Pharmaceuticals) (0.01%-5% drug loading) were prepared as standards for a calibration curve. Given the 10% (w/w) loading of PTX in ABRAXANE®, these standards correspond to 1%-50% relative crystallinity of the PTX, in the assumption that the polymorphic form of PTX used in the calibration curve matches that found in ABRAXANE®.

Raman images were acquired on an alpha300 AR commercial confocal reflectance Raman microscope (WITec) with a 633 nm HeNe source, 35 mW output (Melles Griot). A 10× objective (0.25 NA) was used, giving a beam waist of 0.8 µm and a depth of field of 20 µm. WITec Control 1.60 was used for data collection. Specific fields of view (300 µm×300 µm) containing a region of interest within the bulk powdered sample were first located via SHG, and then marked for subsequent confocal Raman analysis. With the crystalline domain located at the center of the marked 300 µm×300 µm field of view (FOV), re-positioning on the Raman microscope via bright field imaging was quite reproducible, allowing the crystallite to be located via spectral analysis with minimal searching. Each spectrum was acquired with four minute integration time, followed by high-pass digital filtering to remove fluorescence background.

Combined SHG/synchrotron X-ray diffraction (XRD) data were acquired with a custom instrument constructed at the Advanced Photon Source at Argonne National Laboratories, described previously. Synchrotron XRD was acquired at 1 second exposures with a beam energy of 12 keV. 2D diffraction images were used to generate representative powder patterns for both ABRAXANE® (SHG active and inactive areas), as well as pure PTX. XRD patterns were produced through mean-subtracted autocorrelation (AC) of the 2D diffraction image along the azimuthal axis (perpendicular to X-ray beam propagation). This process removes azimuthally static contributions (amorphous scatter) while selectively amplifying spots within the 2D image. As not all crystal orientations are probed in such an analysis, the relative peak height within the AC generated powder patterns is highly sensitive to preferred orientation effects. As a complement, bench top powder X-ray diffraction (PXRD) was acquired on a Rigaku SmartLab™ diffractometer (0.1544 nm wavelength) scanned at one degree/min.

Results and Discussion

FIGS. 1a-1d show SHG images of four different batches (varying lot numbers) of ABRAXANE®. Samples were imaged in powdered form, as received from the manufacturer. All images are shown on the same brightness scale. Insets show line scans across a single particle in each batch in units of millions of photon counts per second (Mcps). High variation in crystallinity and particle number/size between batches is readily observed.

A sample from batch 1 was imaged with SHG both before and after dissolution in ultrapure water, the results of which are shown in FIGS. 2a-2d. This experiment was performed primarily to exclude SHG interferences from the relatively small fraction of buffer salts known to form noncentrosymmetric SHG-active crystals. It would not be unreasonable for such compounds to exist within the formulation given the use of HSA as the matrix. However, all such compounds are highly water soluble and would not be expected to remain following addition of water to the sample. Furthermore, solubilization in water mirrors the recommended procedure in preparation for parenteral introduction. FIGS. 2a-2d summarize these results, showing bright field (FIGS. 2a and 2b) and SHG (FIGS. 2c and 2d) images before and after dissolution in ultrapure water, respectively. SHG active areas remained even after dissolution in ultrapure water combined with vigorous mixing, suggesting that the SHG-active material exhibited poor aqueous solubility and was unlikely to be an SHG-active buffer salt.

Figures 3A, 3B:
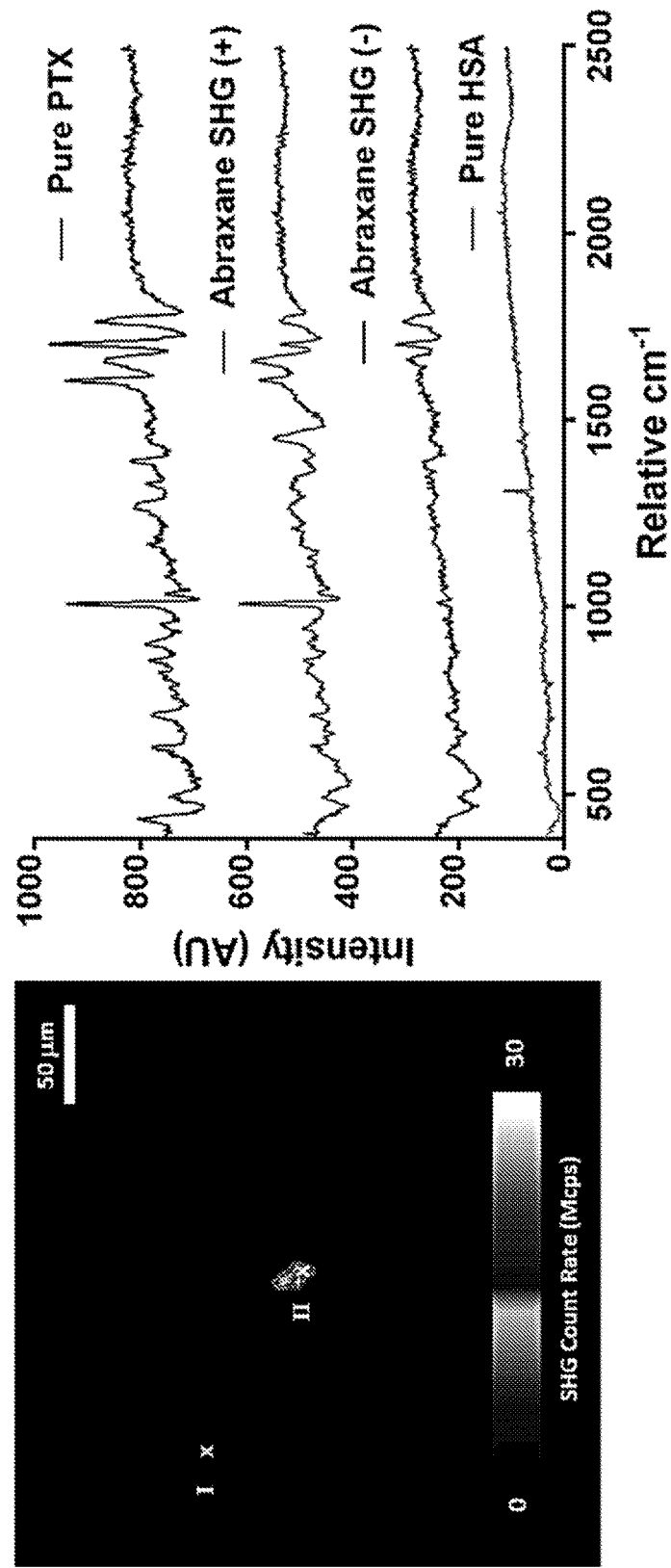
FIG. 3a is a SHG image.
FIG. 3b is a corresponding confocal Raman spectra to the SHG image in FIG. 3a after digital high-pass filtering.

Additional confocal Raman measurements were performed selectively on the regions of interest identified as the SHG-active domains in the native ABRAXANE® dosage form, the results of which are summarized in FIGS. 3a and 3b. With initial screening by SHG, a crystalline domain of interest (~20 µm diameter) within a 300 µm×300 µm FOV was marked for subsequent analysis, shown in FIG. 3a. FIG. 3b summarizes the experimental Raman spectra acquired within the region of interest and elsewhere in the FOV. For comparison, the experimental Raman spectra of pure PTX and pure HSA are also shown. The Raman spectrum acquired from the SHG-active region of interest agrees remarkably well with the measured spectrum of pure crystalline PTX. Furthermore, the peak heights were notably greater in the SHG-active region, consistent with a higher local concentration of PTX relative to other locations within the formulation. In addition, the two peaks at 1006.7 $cm^{-1}$ and 1604.3 $cm^{-1}$ are most pronounced in the crystalline PTX spectrum, as well as in that of the SHG-active region, but are only marginally detectable in other locations within the formulation.

Figures 4A, 4B, 4C, 4D, 4E:
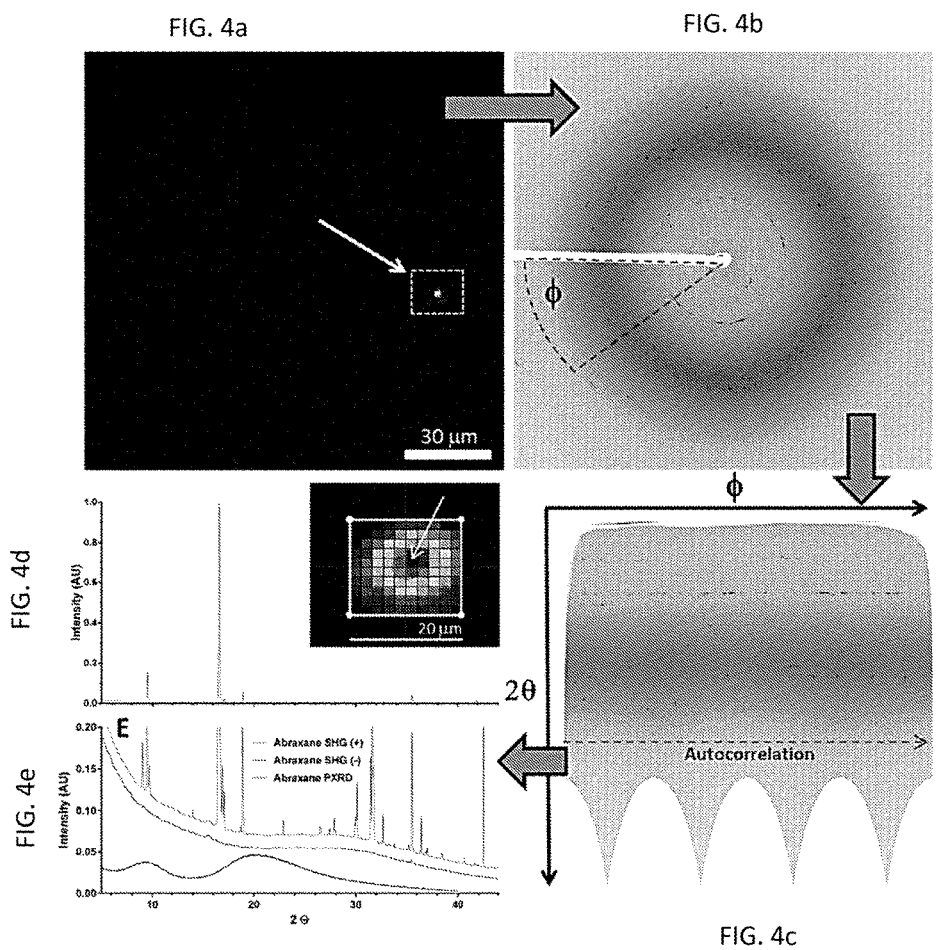
FIG. 4a is a SHG image acquired with the integrated SHG/synchrotron X-ray diffraction (XRD) instrument.
FIG. 4b is an image showing how the X-ray beam can be centered on the SHG active region for subsequent analysis, generating 2D diffraction images.
FIG. 4c is an image showing remapping of the image in FIG. 4b to polar coordinates.
FIG. 4d is the mean-subtracted autocorrelogram (AC) along $\phi$ which generates an equivalent powder pattern for the probed crystallite.
FIG. 4e shows derived powder patterns for SHG active and inactive regions of ABRAXANE®, along with an experimental laboratory instrument pattern for batch 4 of ABRAXANE®, showing only amorphous scatter.

In addition to the confocal Raman spectroscopy measurements, XRD measurements were performed to probe composition and crystal form. Measurements were performed using a bench-top XRD instrument as well as a one-of-a-kind instrument combining SHG imaging and "mini-beam" synchrotron microdiffraction on a single integrated platform described previously. FIGS. 4a-4e summarize the data acquisition and analysis process. Specifically: FIG. 4a is an SHG image acquired with the integrated SHG/synchrotron XRD instrument. After identification of the ROI, the X-ray beam (5 µm diameter) can be centered on the SHG active region for subsequent analysis, generating 2D diffraction images as shown in FIG. 4b. Remapping of FIG. 4b to polar coordinates generates the image in FIG. 4c. Mean-subtracted autocorrelation (AC) along ϕ generates an equivalent powder pattern for the probed crystallite, as shown in FIG. 4d. Inset in FIG. 4d shows an autoscoring of diffraction peaks (blue corresponds to no peaks, red corresponds to the most peaks), with the pattern in FIG. 4d arising from AC of the indicated pixel. FIG. 4e shows derived powder patterns for SHG active and inactive regions of ABRAXANE®, along with an experimental laboratory instrument pattern for batch 4 of ABRAXANE®, showing only amorphous scatter. The red trace in FIG. 4e is the sum of the 20 highest scoring pixels of the inset in FIG. 4d.

Utilizing a "click to center" algorithm, a "mini-beam" (5 µm beam diameter) synchrotron X-ray beam was selectively directed to regions of interest (ROI) identified by SHG (FIG. 4a) on the same instrument, generating 2D scattering patterns (FIG. 4b). Following ROI identification, the X-ray scattering measurements were performed by raster-scanning an X-ray beam over a 20 µm by 20 µm area in 2 µm steps to generate data both coincident and non-coincident with the ROI. FIG. 4c shows the remapping of the 2D diffraction images to polar coordinates for autocorrelation (AC), with results for an SHG active region of ABRAXANE® shown in FIG. 4d. The inset in FIG. 4d shows an autoscoring of diffraction quality for the raster scan, with blue corresponding to no spots and red corresponding to the most spots within the 2D diffraction image. The pattern shown in FIG. 4d is from a single pixel of the inset (pixel indicated). FIG. 4e compares the summed AC powder patterns for SHG active and inactive areas of ABRAXANE® (red and blue traces, respectively). Also shown in FIG. 4e (black trace) is an experimental laboratory PXRD pattern of batch 4 of ABRAXANE®, showing that the observed crystallinity in batch 4 is below the LOD for the laboratory PXRD instrument.

Figure 5:
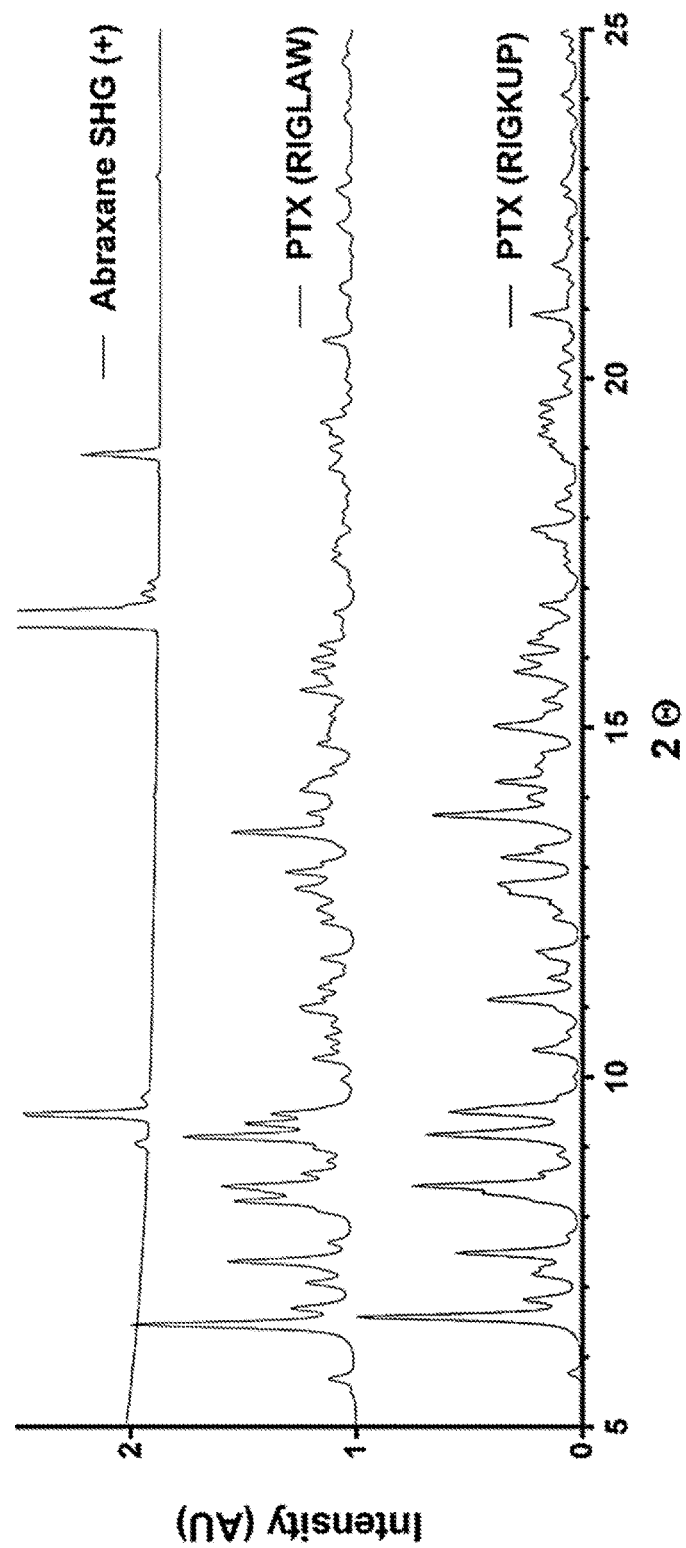
FIG. 5 is a comparison of the experimental AC powder pattern for ABRAXANE® with predicted patterns at 12 keV for the anhydrous and dihydrate forms of PTX from a database.

The measured XRD patterns recovered by azimuthal autocorrelation were compared with the predicted patterns generated from two known PTX structures deposited in the Cambridge Structural Database. Because a finite number of crystals are probed with such a narrow X-ray beam, the experimental measurements clearly exhibit preferred orientation effects, in which the assumption of a statistical average over all crystal orientations and sizes no longer holds. Consequently, the peaks identified by autocorrelation of the scattering images sampled only a subset of the possible peaks satisfying the Bragg condition. Similarly, the relative peak heights can exhibit large variability compared to the predicted powder pattern from preferred orientation. However, the presence of diffraction at particular $2\theta$ angles can still provide information directly related to lattice constants for comparison with the predicted angles, following wavelength normalization. FIG. 5 shows the SHG positive AC powder pattern from FIG. 4e overlaid with a predicted powder pattern at 12 keV (synchrotron beam energy) from the Cambridge Structural Database (CSD) for the anhydrous and dihydrate forms of PTX (CSD IDs: RIGLAW and RIGKUP, respectively). Table I summarizes the comparison between the measured and anticipated diffraction peak locations ($2\theta$) for these three patterns. The large majority of peaks identified by PXRD are in reasonably good agreement with peak locations anticipated based on the two PTX lattices. It should be appreciated that the information in Table 1 serves only to demonstrate that peaks in general in the XRD measurement are able to be observed. Peaks in the $2\theta$ are therefore presented only as demonstrative of the ability to see peaks in the XRD measurement once targeted by SHG.

TABLE 1

Comparison of $2\Theta$ values for peaks present in the AC powder pattern of an SHG active crystallite within ABRAXANE ®

| Abraxane (SHG+) | PTX (RIGLAW) | PTX (RIGKUP) |
| --- | --- | --- |
| 8.98 | 8.98 | 8.88 |
| 9.45 | 9.34 | 9.50 |
| 9.68 | 9.48 | 9.72 |
| 14.0 | 14.0 | 14.0 |
| 16.5 | 16.4 | 16.4 |
| 16.9 | 16.6 | 16.9 |
| 17.0 | 17.0 | 17.0 |
| 18.6 | 18.7 | 18.7 |
| 18.9 | 19.2 | 18.9 |

If the SHG-active and poorly soluble fraction of material in ABRAXANE® is attributed to PTX, SHG microscopy can be used to estimate the relative crystallinity within the formulation. A calibration curve of SHG signal was constructed from physical mixtures of crystalline PTX in HSA at various loadings, accounting for the 10% (w/w) loading of PTX in ABRAXANE®. The PTX within batch 1 was found to be 30±13% (95% CI) crystalline, corresponding to 3.0% overall crystallinity in the measured lot of ABRAXANE®. The relatively large uncertainty in the crystallinity arose primarily from the limited volumes of materials probed, resulting in statistical fluctuations in the crystalline fraction per probed volume. Such a large fraction of PTX present in a crystalline state may potentially impact the effective dose of the formulation.

Figure 6A:
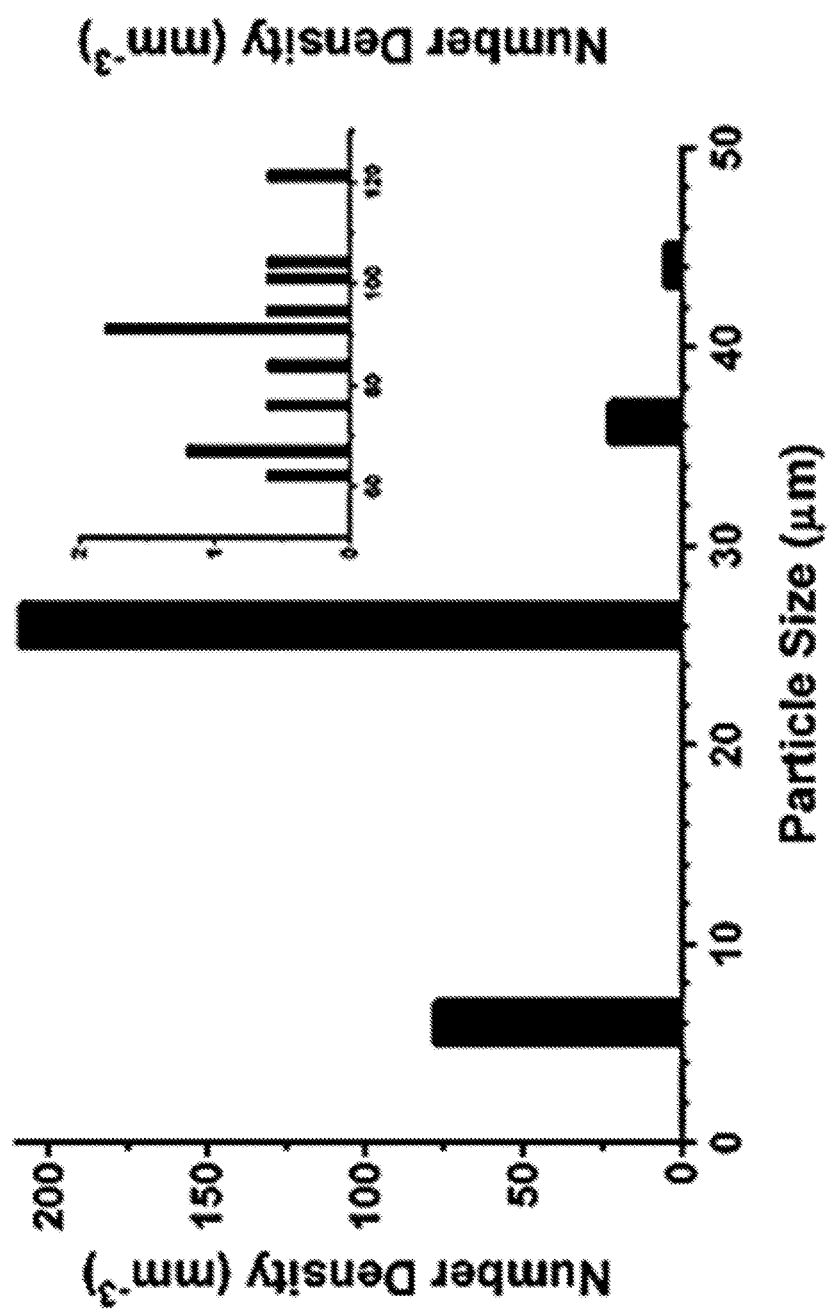
FIG. 6a is a histogram of crystal size for batch 1 of ABRAXANE® with occurrence reported as particle number density.
Figure 6B:
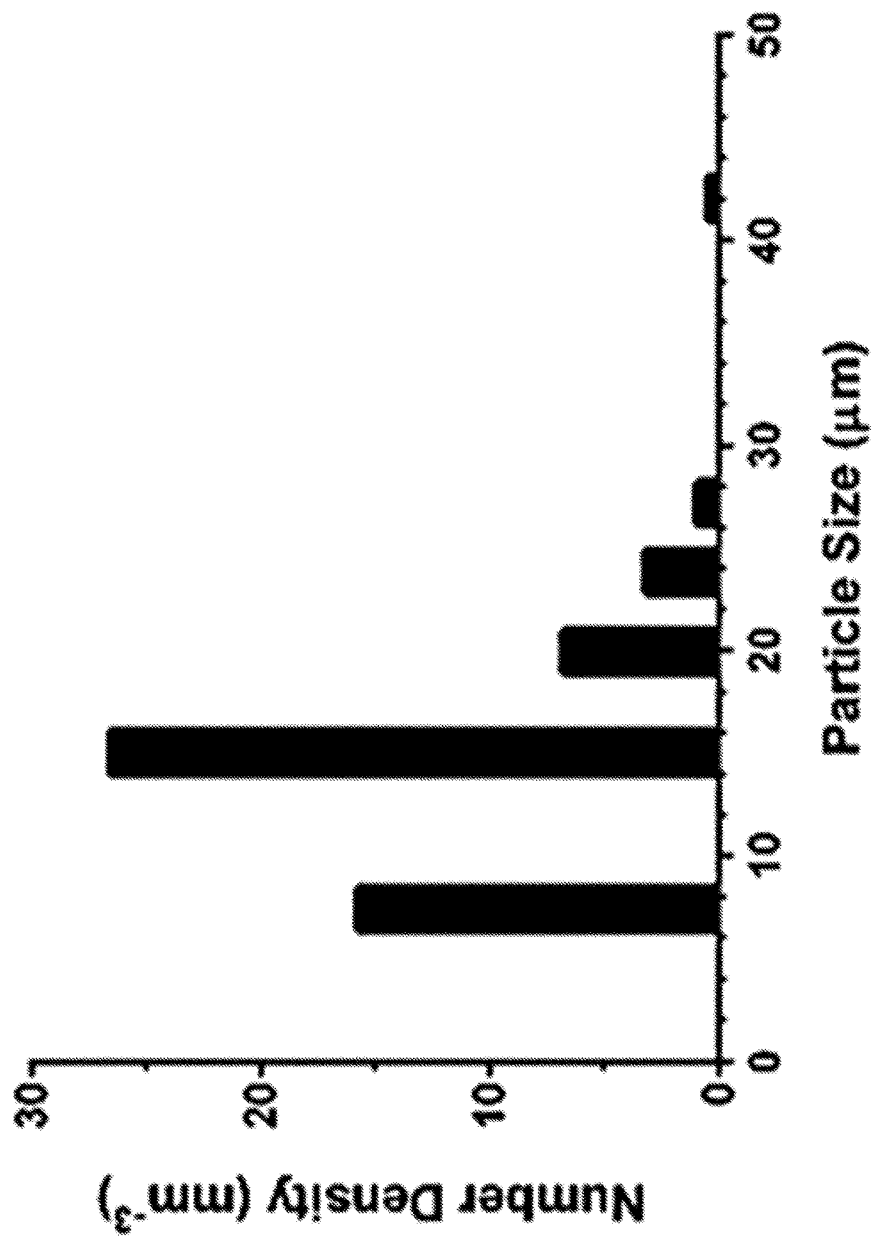
FIG. 6b is a histogram of crystal size for batch 3 of ABRAXANE® with occurrence reported as particle number density.
Figure 6C:
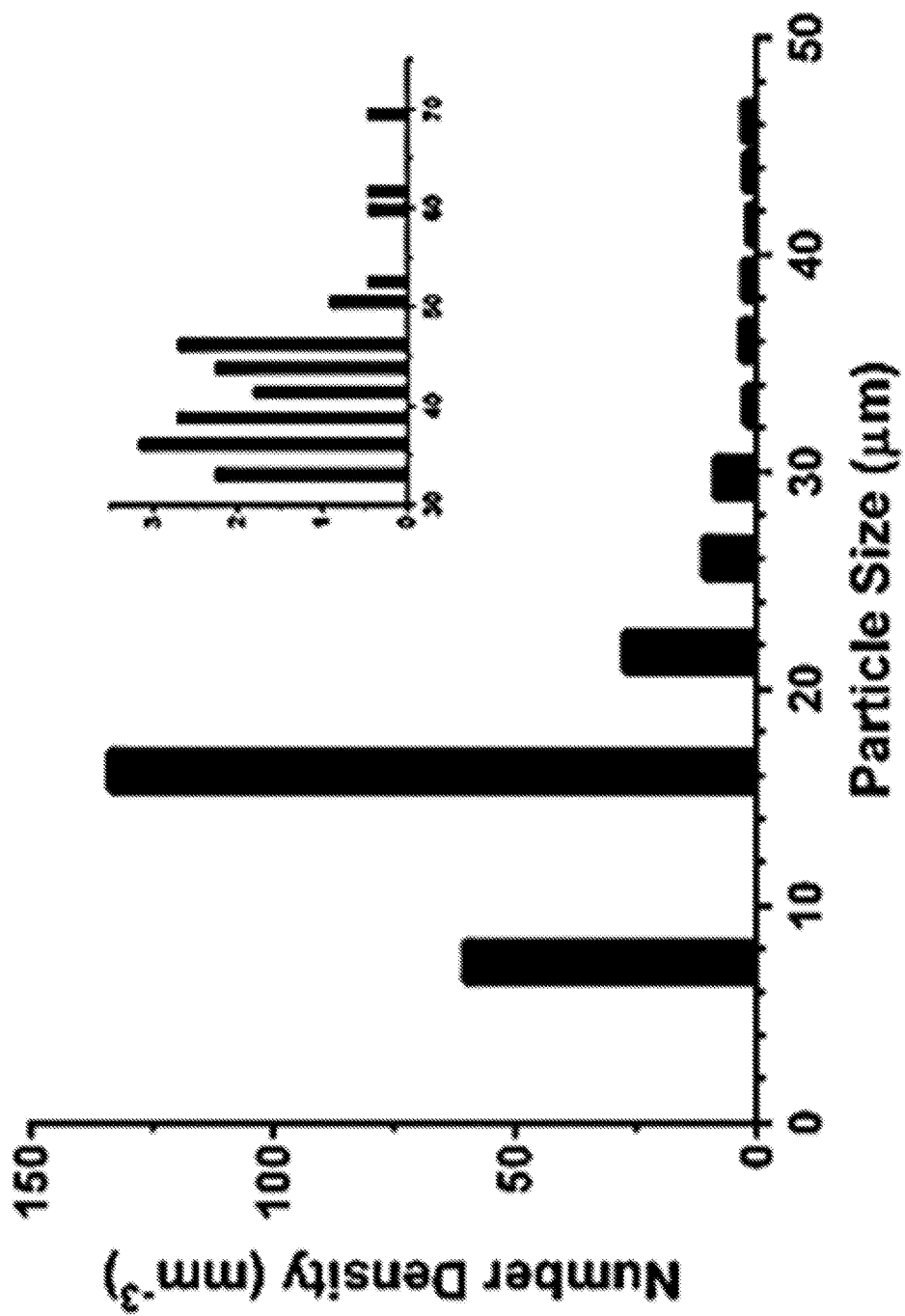
FIG. 6c is a histogram of crystal size for batch 4 of ABRAXANE® with occurrence reported as particle number density.

The spatial information afforded by SHG also allows assessment of the size distribution of poorly soluble particulates in situ within the final dosage forms. Histograms of SHG-active particle sizes are shown in FIGS. 6a-6c for batches 1, 3, and 4 (FIGS. 6a-6c, respectively) as batch 2 did not contain enough particles to produce a meaningful histogram. In brief, different lots exhibited diverse distributions, with particle size ranging from <10 μm to over 120 μm. For comparison, USP-37/NF-32 recommendations on particulates within injectable formulations of less than 100 mL total injection volume requires no more than 3000 particles >10 μm and no more than 300 particles >25 μm be present in the container. As the mass fraction probed by SHG represents approximately 1% of the container contents, the observation of 37 particles greater than 26 μm within the imaged fraction of batch 1 suggests over 3000 particles >25 μm present within the entire container. Direct access to the size distribution of insoluble crystalline particles performed by SHG microscopy would be challenging to obtain in situ within the final dosage form using alternative methods given the optical opacity of the ABRAXANE® formulation, but is straightforward by SHG imaging.

This initial screening by SHG greatly reduced the time required to perform the Raman measurements, as only a small area fraction of the prepared sample (0.25%) was probed in order to obtain the spectra in FIGS. 3a and 3b. Assuming a minimum integration time of 30 seconds/pixel to achieve SNR high enough for crystal identification (integration times of 4 minutes per spectrum were used for the results in FIGS. 3a and 3b), screening of the same bulk area by Raman alone at the same resolution would require nearly 3 years of continuous measurement with the instrument used herein compared to 2 seconds by SHG microscopy, with neither estimate including dead time for sample positioning.

A similar advantage in pre-identification of ROIs by SHG microscopy arises in the synchrotron XRD analysis. While the localized synchrotron XRD produces a high SNR (~20,000 in FIG. 4d) for 1 s acquisitions, the "mini-beam" experiments enabling such a measurement are not amenable to rapid sample analysis. Assuming 1 second integration per pixel and a coarse screen with a 20 μm X-ray beam yields a total analysis time of 33 hours, but with a significantly higher value placed on synchrotron time. However, guiding the XRD to ROIs identified by SHG enables total analysis times on the order of minutes. For comparison, the bench top PXRD pattern in FIG. 4e shows SNR≤1 for a 35 minute acquisition time. Without quantitative knowledge of the SNR, the time required for observation of peaks within the PXRD pattern is difficult to estimate. Assuming SNR=1, observation of peaks would require an integration time >5 hours, although this estimate represents the optimum scenario based on the current data.

Conclusions

Using SHG microscopy to identify regions of interest within amorphous pharmaceutical formulations was found to enable targeted analysis by Raman and XRD. By matching the probed volume more closely to the dimensions of the targeted crystallites, the corresponding reduction in background provided improvements of ~2 decades in the detection limits for trace crystallinity in both Raman and XRD relative to established bench top instruments. Characterization of the amorphous nanosuspension ABRAXANE® illustrated this process for a model drug formulation currently in clinical use. Substantial variability in relative crystallinity was observed within the product as-received, with water-insoluble particles up to 120 μm observed in the formulation. Targeted analysis by XRD and Raman spectroscopy were both consistent with crystalline paclitaxel comprising the insoluble particles. These combined results highlight the potential benefits provided by the marriage of the rapid and highly selective technique of SHG with information-rich methods such as Raman and XRD.

Those skilled in the art will recognize that numerous modifications can be made to the specific implementations described above. The implementations should not be limited to the particular limitations described. Other implementations may be possible.

The invention claimed is:

1. A method for identifying composition, the method comprising:
    acquiring at least one second harmonic generation (SHG) image of a sample;
    analyzing the at least one SHG image to obtain at least one field of view;
    generating a plurality of particle histograms from the at least one field of view;
    locating at least one region of interest within the at least one field of view of the at least one SHG image;
    acquiring at least one Raman spectrum from the at least one region of interest;
    assessing composition of an individual particle via spectral analysis of the at least one Raman spectrum;
    acquiring at least one x-ray diffraction (XRD) image from the at least one region of interest;
    producing a representative powder pattern of the individual particle from the at least one XRD image; and
    comparing the representative powder pattern with a set of powder patterns from a database to validate composition of the individual particle.

2. The method of claim 1, wherein the representative power pattern is produced using mean-subtracted autocorrelation of the XRD image along an azimuthal axis.

3. The method of claim 1, further comprising collecting SHG light in the transmission direction.

4. A method for identifying composition of an individual particle, the method comprising:
    acquiring at least one second harmonic generation (SHG) image of a sample;
    analyzing the at least one SHG image to obtain at least one field of view;
    generating a plurality of particle histograms from the at least one field of view;
    locating at least one region of interest within the at least one field of view of the at least one SHG image;
    acquiring at least one Raman spectrum from the at least one region of interest;
    assessing composition of the individual particle via spectral analysis of the at least one Raman spectrum; and
    determining composition of the individual particle.

5. The method of claim 4, wherein the determining composition of the individual particle comprises: comparing a Raman spectrum of the individual particle with a reference spectrum from a database to validate composition of the individual particle.

6. A method for identifying composition of an individual particle, the method comprising:
    acquiring at least one second harmonic generation (SHG) image of a sample;
    analyzing the at least one SHG image to obtain at least one field of view;
    generating a plurality of particle histograms from the at least one field of view;
    locating at least one region of interest within the at least one field of view of the at least one SHG image;
    acquiring at least one x-ray diffraction (XRD) image from the at least one region of interest;
    assessing composition of the individual particle via spectral analysis of the at least one XRD image; and
    determining composition of the individual particle.

7. The method of claim 6, wherein the determining composition of the individual particle comprises: comparing an X-ray spectrum of the individual particle with a reference spectrum from a database to validate composition of the individual particle.

8. The method of claim 7, wherein the x-ray spectrum of the individual particle is produced using mean-subtracted autocorrelation of the XRD image along an azimuthal axis.

* * * * *